US008180654B2

(12) United States Patent
Berkman et al.

(10) Patent No.: US 8,180,654 B2
(45) Date of Patent: May 15, 2012

(54) METHOD AND SYSTEM FOR CREATING, ASSEMBLING, MANAGING, UTILIZING, AND SECURELY STORING PORTABLE PERSONAL MEDICAL RECORDS

(75) Inventors: Seth M. Berkman, Ossining, NY (US); Gregory J. Rosensteel, White Plains, NY (US); Merle J. Bushkin, Hartsdale, NY (US)

(73) Assignee: Health Record Corporation, Brownsville, VT (US)

( * ) Notice: Subject to any disclaimer, the term of this patent is extended or adjusted under 35 U.S.C. 154(b) by 889 days.

(21) Appl. No.: 11/930,510

(22) Filed: Oct. 31, 2007

(65) Prior Publication Data

US 2009/0112627 A1 Apr. 30, 2009

(51) Int. Cl.
*G06Q 50/00* (2012.01)
(52) U.S. Cl. .......................................................... 705/3
(58) Field of Classification Search ................... 705/2–4
See application file for complete search history.

(56) References Cited

U.S. PATENT DOCUMENTS

| | | | |
|---|---|---|---|
| 6,513,720 B1 | 2/2003 | Armstrong | |
| 6,747,561 B1 | 6/2004 | Reeves | |
| 7,273,454 B2* | 9/2007 | Raymond et al. | 600/301 |
| 7,395,215 B2* | 7/2008 | Grushka | 705/2 |
| 7,716,072 B1* | 5/2010 | Green et al. | 705/3 |
| 7,899,687 B2* | 3/2011 | Morris | 705/3 |
| 2004/0186746 A1* | 9/2004 | Angst et al. | 705/3 |
| 2004/0236680 A1* | 11/2004 | Luoffo et al. | 705/39 |
| 2005/0043827 A1* | 2/2005 | Schaeffer et al. | 700/72 |
| 2005/0108059 A1* | 5/2005 | Tay | 705/3 |
| 2005/0187797 A1* | 8/2005 | Johnson | 705/3 |
| 2006/0036471 A1* | 2/2006 | Sanjay-Gopal et al. | 705/3 |
| 2006/0074713 A1* | 4/2006 | Conry et al. | 705/2 |
| 2006/0080137 A1 | 4/2006 | Chambers | |
| 2006/0241977 A1* | 10/2006 | Fitzgerald et al. | 705/3 |
| 2007/0016450 A1 | 1/2007 | Bhora | |
| 2008/0027752 A1 | 1/2008 | Phan | |
| 2008/0288281 A1* | 11/2008 | Shell et al. | 705/2 |
| 2009/0076849 A1* | 3/2009 | Diller | 705/3 |

OTHER PUBLICATIONS

Yasnoff "Exposing the Myths of Health Information Infrastructure" Aug. 27, 2006.

(Continued)

*Primary Examiner* — Gerald J. O'Connor
*Assistant Examiner* — Mark Holcomb
(74) *Attorney, Agent, or Firm* — Rajesh Vallabh; Foley Hoag LLP

(57) ABSTRACT

A method and system are provided for utilizing indexed electronic patient medical records stored on portable memory devices. Each of the portable memory devices is associated with a patient for electronically storing indexed medical records for the patient from a plurality of care providers. The indexed medical records are sortable or searchable. For each visit to a care provider by a patient, the method includes: (a) accessing the indexed medical records from a portable memory device associated with the patient; (b) automatically generating one or more documents for use during the visit from the indexed medical records; (c) providing medical services to the patient utilizing the indexed medical records and the one or more documents; (d) recording information relating to the medical services on the one or more documents, and loading the information on the portable memory device; and (e) sending delayed information relating to the medical services to a remote server for subsequent downloading by the patient or another authorized person of the delayed information from the server to the portable memory device.

29 Claims, 10 Drawing Sheets

OTHER PUBLICATIONS

"CapMed Offers Software Applications to Help Patients Track and Manage Their Health", Press Release (publication date unknown).

"Having Key Data Ready in an Emergency" Wall Street Journal, Jul. 27, 2004; p. D1.

"Portable Medical Data Moves Beyond Discussion Phase", Press Relase, (publication date unknown).

Rainey "Portable Health Record Attracts Hospital Groups" Business Ledger (publication date unknown).

"Medical Record", Wikipedia, (publication date unknown).

"CapMed Selected by Microsoft to Offer in Case of Emergency (ICE) Personal Health Record to Millions Through Microsoft HealthVault Platform" Press Release, Oct. 4, 2007.

http://www.healthtechservices.com/MTHome.html, Health Tech Services Medictag, Date of Original Publication Unknown.

http://www.micardinc.com/, MiCARD, Date of Original Publication Unknown.

http://www.vitalkey.com/, Vital Key, Date of Original Publication Unknown.

http://vitalrecord.net/, The Vital Record Corporation; Med Records to Go, Date of Original Publication Unknown.

Stacy Lawrence, "Portable EMRs Are Still to Come", eWeek.com, Mar. 3, 2005.

"Thousands of Patients Have Their Own Portable Medical Records", Medical Informatics News, ChartWare Inc., Jul. 24, 2006.

http://www.walletex.com, Walletex Microelectronics, Date of Original Publication Unknown.

http://www.medicalert.org/home/HomeProductCatalogs.aspx, Medic Alert, Date of Original Publication Unknown.

http://www.medkey.com/medkey.html, MedKey, Date of Original Publication Unknown.

http://patientpassport.com/services/, Patient Passport, Date of Original Publication Unknown.

Kennedy, Kyle, A Stick In Time: Businessmen Create Device That Holds Medical Information, The Ledger Mar. 13, 2008.

* cited by examiner

Patient Health Summary
(Before Examination)

Date: 07/21/07
Patient: John Doe

Problems:
    Arthritis- Fingers                     1998
    Cervical Osteoarthritis-Radiculitis  1995
    Tendency towards Gout        1970
    New_____
    New_____
    New_____

Current Medications:
    Allopurinol      300mg Daily    Silver
    Ketaconazole cream  2.0%         Blue
    New_____
    New_____
    New_____

Allergies:
    Tetracycline    Rash
    New_____

Encounters:

| Date: | Issue: | Care Provider: |
|---|---|---|
| 04/27/07 | Eye exam | Dr. Red |
| 04/18/07 | Annual Physical | Dr. Silver |
| 11/03/06 | Sore Throat | Dr. Silver |
| 09/13/05 | Rash | Dr. Blue |
| 09/13/05 | Rash | Dr. Blue |
| 05/12/05 | Annual Physical | Dr. Silver |
| 03/09/05 | Ophthalmology | Dr. Red |
| 01/05/05 | Post-op Exam | Dr. White |
| 10/21/04 | Pre-op Exam | Dr. Silver |

Patient Health Summary
(After Examination)

Date: 07/21/07
Patient: John Doe

Problems:
    Arthritis- Fingers                       1998
    Cervical Osteoarthritis-Radiculitis   1995
    Tendency towards Gout           1970
    New_____
    New_____
    New_____

Current Medications:
    Allopurinol     300mg Daily    Silver
    ~~Ketaconazole cream~~  ~~2.0%~~    ~~Blue~~
    Motrin         600 mg         qId
    New_____
    New_____

Allergies:
    Tetracycline    Rash
    New_____

Encounters:

| Date: | Issue: | Care Provider: |
|---|---|---|
| 04/27/07 | Eye exam | Dr. Red |
| 04/18/07 | Annual Physical | Dr. Silver |
| 11/03/06 | Sore Throat | Dr. Silver |
| 09/13/05 | Rash | Dr. Blue |
| 09/13/05 | Rash | Dr. Blue |
| 05/12/05 | Annual Physical | Dr. Silver |
| 03/09/05 | Ophthalmology | Dr. Red |
| 01/05/05 | Post-op Exam | Dr. White |
| 10/21/04 | Pre-op Exam | Dr. Silver |

Patient Encounter Summary
(Before Examination)

| | |
|---|---|
| Date: 07/21/07<br>Patient: John Doe<br>CC: Pain left ankle s/p surgery | Anatomical Loc:<br>☐ HEAD<br>☐ Neck<br>☐☐ Shoulder<br>☐☐ Arm<br>☐☐ Elbow<br>☐☐ Forearm<br>☐☐ Hand<br>☐ Thorax<br>☐ Abdomen<br>☐ Back<br>☐ Pelvis<br>☐ Perineum<br>☐ Genitalia<br>☐☐ Hip<br>☐☐ Thigh<br>☐☐ Knee<br>☐☐ Ankle<br>☐☐ Foot<br><br>System:<br>☐ Cardiovascular<br>☐ Circulatory<br>☐ Endocrine<br>☐ Gastrointestinal<br>☐ Immune<br>☐ Integumentary<br>☐ Lymphatic<br>☐ Musculoskeletal<br>☐ Nervous<br>☐ Reproductive<br>☐ Urinary<br><br>ICD:<br>☐☐☐☐☐<br>☐☐☐☐☐<br>☐☐☐☐☐<br>CPT:<br>☐☐☐☐☐<br>☐☐☐☐☐<br>☐☐☐☐☐ |
| HPI: | |
| VS: BP    HR    Resp    Temp | |
| PE: | |
| Assessment: | |
| Plan: | |
| X: | |

Patient Encounter Summary
(After Examination)

| | |
|---|---|
| Date: 07/21/07<br>Patient: John Doe<br>CC: Pain left ankle s/p surgery | Anatomical Loc:<br>☐ HEAD<br>☐ Neck<br>☐☐ Shoulder<br>☐☐ Arm<br>☐☐ Elbow<br>☐☐ Forearm<br>☐☐ Hand<br>☐ Thorax<br>☐ Abdomen<br>☐ Back<br>☐ Pelvis<br>☐ Perineum<br>☐ Genitalia<br>☐☐ Hip<br>☐☐ Thigh<br>☐☐ Knee<br>x☐ Ankle<br>☐☐ Foot<br><br>System:<br>☐ Cardiovascular<br>☐ Circulatory<br>☐ Endocrine<br>☐ Gastrointestinal<br>☐ Immune<br>☐ Integumentary<br>☐ Lymphatic<br>x Musculoskeletal<br>☐ Nervous<br>☐ Reproductive<br>☐ Urinary<br><br>ICD:<br>46200<br>☐☐☐☐☐<br>☐☐☐☐☐<br>CPT:<br>99213<br>☐☐☐☐☐<br>☐☐☐☐☐ |
| HPI: 60 y/o male complains of continued left ankle pain s/p ankle stabilization surgery. He complains of swelling increasing during each day and pain on ambulation. | |
| VS: BP 120/80  HR 70    Resp 16  Temp 37.0 | |
| PE:<br>HEENT: Normal cephalic, eyes clear, canal OM clear<br>Neck: Normal ROM<br>Chest: Normal BBS, no wheezes or rales<br>COR: RRR no murmurs<br>Adb: Soft non-tender, normal BS<br>Ext: Left ankle swelling, 2+, tender diffusely about the joint | |
| Assessment: L Ankle Inflammation s/p stabilization | |
| Plan: Elevate, ice and Motrin 600 mg qld | |
| X: Silver | |

MedKaz™ Lifetime Health Record medkaz — Lifetime Health Record™

Name: John Doe  
Nickname:  
Gender: Male  
Date of Birth: 03/21/1935  
Age: 72  
Language: English  
Nationality: American Height: 6' 3"  
Weight: 212  
Eyes: Brown  
Hair: Grey  
Blood Type: O+  
Medical Devices: Hearing aids

ALERT!  
Illnesses: Arthritis in neck, Rheumatic fever as child  
Surgeries: Jaw resection, Left ankle - arthroscopy  
Allergies: Tetracycline  
Medications: Allopurinol

Doctors - Dentists Hospitals

| | Date | Practitioner | Specialty | Reason/Complaint | CPT | Assessment/Procedure | ICD-9-CM Co | Document Type | Anatomical Loc | System |
|---|---|---|---|---|---|---|---|---|---|---|
| | 04/27/2007 | Allen, XXXXX, MD | Opthalmology | Near sighted; Astigmatism | | Continue wearing glasses | | Notes | Eyes | |
| | 04/18/2007 | Michael, XXXXX, MD | Cardiology & Internal Medicine | Annual Physical | | Acvil/Exercise for Tendonitis in left | 726.1 | | Left Shoulder | Musculoskeletal |
| | 11/3/2006 | Michael, XXXXX, MD | Cardiology & Internal Medicine | Sore throat/fatigue/ malaise | 99213 | Pharyngitis | 462 | Notes | Throat | |
| | 9/13/2005 | Marc, XXXXX, MD | Dermatology | Spots on skin | | Seborrheic Keratosis | | Notes | Forehead/Chest /Rt. Foot | |
| | 9/13/2007 | Marc, XXXXX, MD | Dermatology | Past Medical History | | | | Notes | | |
| | 5/12/2005 | Michael, XXXXX, MD | Cardiology & Internal Medicine | Annual Physical | | Advised wt. loss; have ear wax removed | | Notes | | |
| | 3/9/2005 | Allen, XXXXX, MD | Opthalmology | Near sighted; Astigmatism | | Continue wearing glasses | | Notes | Eyes | |
| | 04/5/2005 | Colleen, XXX, MD | Orthopedic Surgery | Post op follow-up | | Ankle healed | | Notes | Left Ankle | Musculoskeletal |
| | 11/24/2004 | Colleen, XXX, MD | Orthopedic Surgery | Post op follow-up | | Mild swelling | | Notes | Left Ankle | Musculoskeletal |
| | 11/4/2004 | Mirjam, XXX, NP, RNFA | FNP | Post surgical exam | | | | Notes | Left Ankle | Musculoskeletal |
| | 10/27/2004 | Colleen, XXX, MD | Orthopedic Surgery | Sergery | | Left ankle: arthroscopy, chondroplasty and excision of loose bodies | | Medical History/ Physical Exam/ Operative Report | Left Ankle | Musculoskeletal |
| | 10/21/2004 | Michael, XXXXX, MD | Cardiology & Internal Medicine | Pre Op Exam | | Cough | | Notes | Lungs | Pulmonary |
| | 10/19/2004 | Colleen, XXX, MD | Orthopedic Surgery | Left ankle pain | | Fracture osteochondral of talus/recommended arthroscopy of left ankle | | Notes | Left Ankle | Musculoskeletal |
| | 10/13/2004 | Eric, XXXXX, MD | Orthopedic Surgery | Left ankle pain | | Detached osteochondral lesion | | Letter | Left Ankle | Musculoskeletal |

702, 704

Encounters  
Doctors - Dentists Hospitals  
Tests - Labs & Images  
Pharmacies & Physical Therapy (Home) (Add Record)

700

METHOD AND SYSTEM FOR CREATING, ASSEMBLING, MANAGING, UTILIZING, AND SECURELY STORING PORTABLE PERSONAL MEDICAL RECORDS

BACKGROUND

1. Field of the Invention

The present application generally relates to personal medical records and, more particularly, to portable personal medical records and a method and system for creating, assembling, managing, utilizing, and securely storing such records.

2. Related Art

A patient's medical record is a documentation of his or her medical history and care; it may include documentation of single or multiple encounters, with one or more care providers. Medical records are known by various names, including among others: patient charts, personal health records (PHRs), health care records, lifetime health records (LHRs), electronic health records (EHRs), and electronic medical records (EMRs). A medical record typically includes some or all of the following patient information and documentation: identification, insurance coverage, employment, family medical history, health history (including illnesses, surgeries and chronic diseases), medications, allergies, immunizations, lab and diagnostic test results, complaints or problems, medical examination assessments and findings, and treatment plans, including referrals to other care providers, medical prescriptions, patient instruction for self-care and return visits. As used herein, care providers include: physicians, dentists, nurses, physician assistants, nurse practitioner, therapists, emergency care personnel, pharmacists, and other medical personnel, as well as personnel working under their direction. They generally deliver their services from health care facilities, including among others: physician offices, healthcare clinics, hospitals including emergency departments, emergency vehicles, labs, pharmacies, physical therapy facilities and nursing homes. The information contained in a medical record allows care providers to provide continuity of care to a patient. The medical record also serves as a basis for documenting the care and services provided to the patient by the care provider, planning patient care, and documenting communication between the care provider and any other health professional contributing to the patient's care.

Patient medical records traditionally are compiled and maintained by individual care providers in their own chosen formats and filed in their own respective repositories or "silos" (they are referred to as silos because they are not connected in any way). Since patients typically see and are treated by more than one care provider throughout their lifetime, their records generally are dispersed among care providers in different practices, hospitals, cities and even states, and generally in disparate, incompatible formats (e.g., handwritten, transcribed, and/or electronic formats). There ordinarily is no single system that consolidates these disparate and dispersed records into a single comprehensive personal lifetime health record for the patient so care providers rarely if ever can access a patient's complete personal health record. Similarly, health insurers have records of reimbursement payments made to care providers for each insured, which indicate the category of service for which they request payment but these records do not describe the complaint or possible alternate diagnoses or other detailed clinical information useful to care providers. Additionally, if the patient has been insured by more than one company, there is no consolidated record for the patient. Finally, health insurer patient medical records generally are available online to the insured patient for only for a limited period of time (e.g., typically one or two years) before they are removed.

Having ready access to a patient's comprehensive lifetime health record (i.e., copies of records from all care providers who have treated the patient spanning a significant period time, perhaps even the patient's lifetime) would allow care providers to better understand the patient's medical history and condition and thereby provide better medical care to the patient. Lack of easy, timely access to such a lifetime health record can lead to costly medical errors such as misdiagnoses, incorrect treatments, unnecessary or redundant medical testing, and prescribing conflicting medications.

BRIEF SUMMARY OF EMBODIMENTS OF THE INVENTION

In accordance with one or more embodiments of the invention, a method is provided for utilizing indexed electronic patient medical records stored on portable memory devices. Each portable memory device is associated with a patient for electronically storing indexed medical records for the patient from a plurality of care providers. The indexed medical records are sortable or searchable electronically. For each visit to a care provider by a patient, the method includes: (a) accessing the indexed medical records from a portable memory device associated with the patient; (b) automatically generating one or more documents for the visit from the indexed medical records; (c) providing medical services to the patient utilizing the indexed medical records and the one or more documents; (d) recording information relating to the medical services on the one or more documents or different documents, and loading the information on the portable memory device; and (e) sending delayed information relating to the medical services to a remote server for subsequent downloading by the patient or another authorized person of the delayed information from the server to the portable memory device.

In accordance with one or more embodiments of the invention, a method is provided for managing portable patient medical records. The method includes (a) providing a portable memory device to each of a plurality of patients for electronically storing indexed medical records for the patient from a plurality of care providers and generating one or more documents from the indexed medical records; and (b) for each visit to a care provider by a patient: (i) receiving from the care provider delayed information relating to medical services provided by the care provider to the patient; and (ii) transmitting the delayed information to a computer operated by the patient or another authorized person for subsequent downloading of the delayed information by the patient or another authorized person from the computer to the portable memory device of the patient.

In accordance with one or more embodiments of the invention, a system is provided for managing portable patient medical records. The system includes a plurality of portable memory devices, each to be provided to one of a plurality of patients. The portable memory devices electronically store indexed medical records for patients from a plurality of care providers and automatically generate one or more documents from the indexed medical records. The system also includes a computer server that receives delayed information from the plurality of care providers for each visit by a patient to a care provider. The delayed information relates to medical services provided to the patient by the care provider. The computer server transmits the delayed information to a computer operated by the patient or another authorized person for subsequent downloading of the delayed information by the patient or another authorized person from the computer to the portable memory device.

Various embodiments of the invention are provided in the following detailed description. As will be realized, the invention is capable of other and different embodiments, and its several details may be capable of modifications in various respects, all without departing from the invention. Accordingly, the drawings and description are to be regarded as illustrative in nature and not in a restrictive or limiting sense, with the scope of the application being indicated in the claims.

BRIEF DESCRIPTION OF THE DRAWINGS

FIGS. 4A and 4B are illustrations of an exemplary patient health summary record before and after examination, respectively, in accordance with one or more embodiments of the invention.

FIGS. 5A and 5B are illustrations of an exemplary medical encounter report form before and after examination, respectively, in accordance with one or more embodiments of the invention.

FIG. 7 is an exemplary screenshot illustrating information displayed to a user accessing encounter information from the portable memory device in accordance with one or more embodiments of the invention.

DETAILED DESCRIPTION

The present invention relates generally to a method and system for creating, managing, utilizing, and securely storing portable personal medical records. Briefly, in accordance with various embodiments of the invention, copies of care provider patient medical records are aggregated, organized and securely stored on portable memory devices kept and controlled by the patients. The portable memory device accepts and stores patient medical records in generally whatever format the patients' care providers use, and is cross-platform compatible, private, and secure. At each encounter with a care provider, the patient presents the portable memory device to the care provider or staff member so the care provider has access to the patient's comprehensive medical record at the time of treatment. At the conclusion of the visit, the patient's medical records stored on the portable memory device are updated by the care provider or staff member with information from the visit so the patient's medical records are kept current. Any delayed data available from a care provider after the visit (e.g., the physician's transcribed notes, diagnostic test results, radiology reports, etc.) can be uploaded by the care provider or his or her staff member (via the Internet or other communication channel) to a remote server and subsequently downloaded by the patient onto the portable memory device.

A care provider treating a patient carrying the portable memory device can thereby immediately access, sort, and search the patient's comprehensive medical records (including current medications, allergies, immunizations, care provider notes, reports, test results, images, contacts, advance directives, etc.) when and where they see the patient, and can avoid costly medical mistakes and unnecessary tests.

Figure 1:
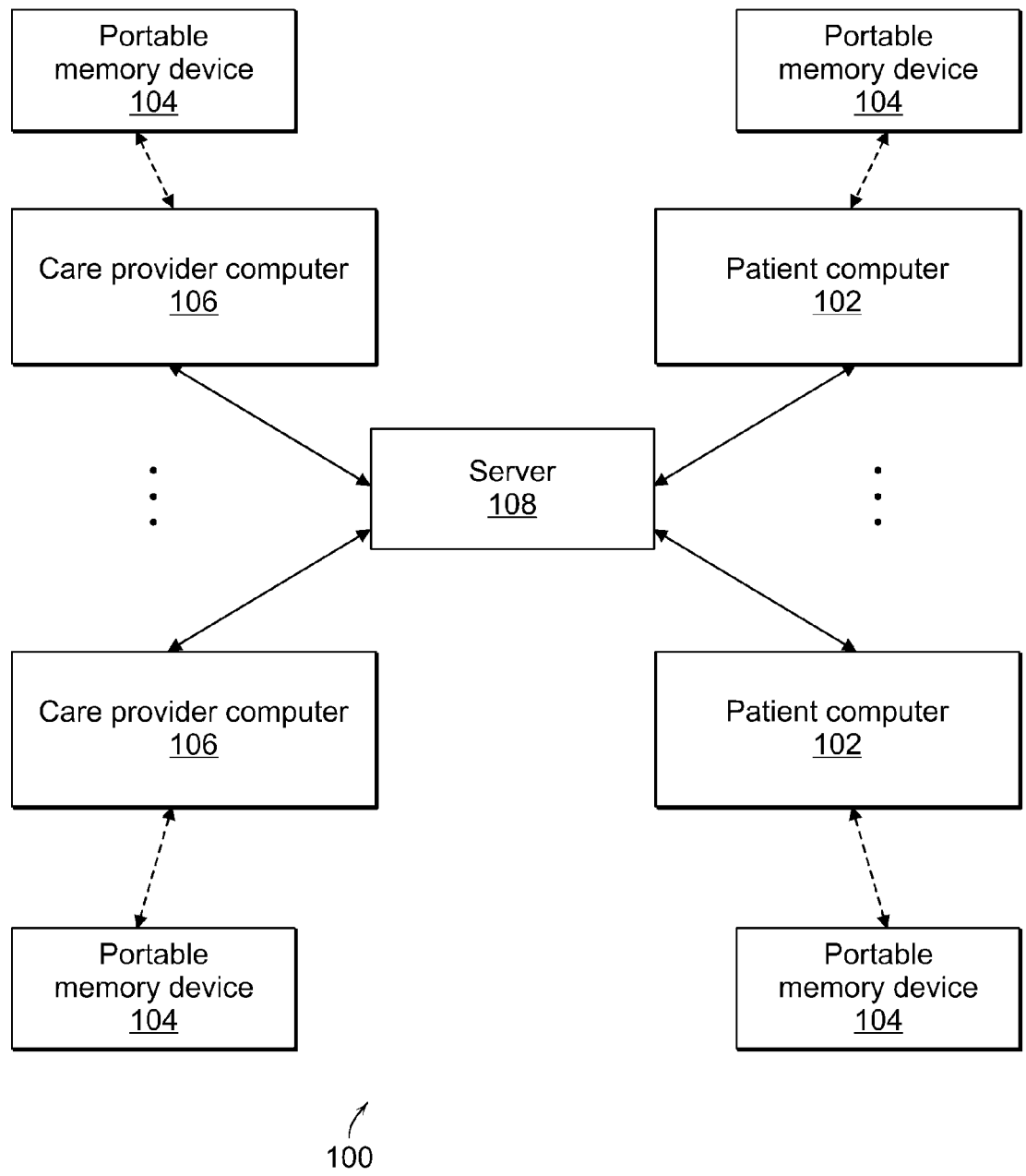
FIG. 1 is a simplified block diagram illustrating a portable medical record management system in accordance with one or more embodiments of the invention.

FIG. 1 is a block diagram schematically illustrating a personal medical record management system 100 in accordance with one or more embodiments of the invention. The system includes a plurality of patient computer systems 102 and portable medical record devices 104, each associated with one of a plurality of patients using the system. The system also includes a plurality of care provider computer systems 106, each associated with one of a plurality of care providers using the system 100. The system 100 further includes one or more remote server computer systems 108 linked by a communication channel to the care provider computer systems 106 and to the patient computer systems 102. The channel may, e.g., be the Internet, an intranet, extranet, local area network, wide area network, Metropolitan area network, or other network connection, and may be wired or wireless.

The care provider computer systems 106 and the patient computer systems 102 can comprise, e.g., one or more personal computers or workstations. Such computers are known to include a processor (e.g., an Intel Pentium processor) running an operating system (e.g., Windows, Mac OS, or Linux), a storage medium readable by the processor (including, e.g., volatile and non-volatile memory and/or storage elements), at least one input device (e.g., a keyboard and mouse), and at least one output device such as a display interface (a graphical user interface or "GUI"). The computer systems 102, 106 also include a standardized or commonly used interface, to which a portable medical device 104 can be connected directly or indirectly and through which data can be transferred between the portable medical device 104 and the computer. A variety of standardized interfaces can be used, including but not limited to, a universal serial port such as USB, Firewire, Serial/RS-232 ports, and wireless transmitters/receivers. The care provider computer systems 106 and the patient computer systems 102 also include several software applications, e.g., Web browsers (such as, Microsoft Internet Explorer or Mozilla Firefox) used to access the Internet, and other applications to create, read, and display different types of files such as, e.g., a data management system, Adobe Acrobat Reader to read PDF files and other applications described below.

The care provider computer systems 106 also preferably include patient record manager software to manage electronic patient medical records. The care provider's patient record manager enables care providers to electronically access, manage, sort and search patient medical records that they create for each patient, upload new records to the patient's portable medical device 104 and store them on the care provider's computer system 106. The records are preferably stored in a manner such that they can be readily imported into another electronic medical record application at a later time, if desired. The care provider computer system can include a plurality of networked personal computers or workstations. The care provider's patient record manager allows medical information for patients to be aggregated from all workstations or computers in the care provider computer system. The care provider's patient record manager then updates the patient's memory device 104 or communicates a patient's medical record to the server 108, which allows the patient to synchronize information with that on his or her memory device 104. The care provider computer systems 106 can also include one or more preferably free-standing computers that can be used for backing up data from memory devices 104 as will be discussed further below.

The server computer system 108 can include a Web server hosting one or more Web sites. A Uniform Resource Locator (URL) identifies a network path to Web pages maintained by the server 108. As is well-known, clients (such as the patient and care provider computer systems 102, 106) communicate with servers via the World Wide Web using the Hypertext Transfer Protocol (HTTP). In turn, the Web server provides users access to files (which can be in different formats such as text, graphics, images, sound, video, etc.) using, e.g., a standard page description language known as Hypertext Markup Language (HTML). Patient data stored on the server computer system 108 are preferably encrypted and password-controlled. As will be described below, the server computer system 108 preferably provides only transient (i.e., temporary) storage of individual patient records. Accordingly, data losses are minimized if the server security is somehow breached.

As will be described in further detail below, the server computer system 108 performs a number of functions, including synchronizing of patient data between the portable memory device 104 and care provider computer systems 106. In addition, the server computer system 108 delivers software updates to the portable memory devices 104, preferably automatically. Additionally, server computer system 108 preferably receives and processes business, technical and marketing data from the portable memory devices 104. The server computer system 108 can be integrated with an accounting system, which keeps track every time care providers, patients and/or others access, upload information to or download information from the patient's portable memory device 104 or the server computer system 108, for accounting, billing and management reporting purposes. In addition, the server computer system 108 is preferably integrated with a secure public web interface, which allows authorized users to easily upload and access information stored on the server 108.

The server computer system can integrate with various third party services and applications including, e.g., the NPI (National Provider Identifier) Database (which provides a listing of licensed care providers), a prescriptions database and/or communication networks (such as, e.g., SureScripts), an instant medical history application stored on the portable memory devices 104, third party EMR HL7 integrators (translators of EMR output for input to portable memory devices), and lab results integration applications from laboratories such as, e.g., Quest and LabCorp.

Figure 2:
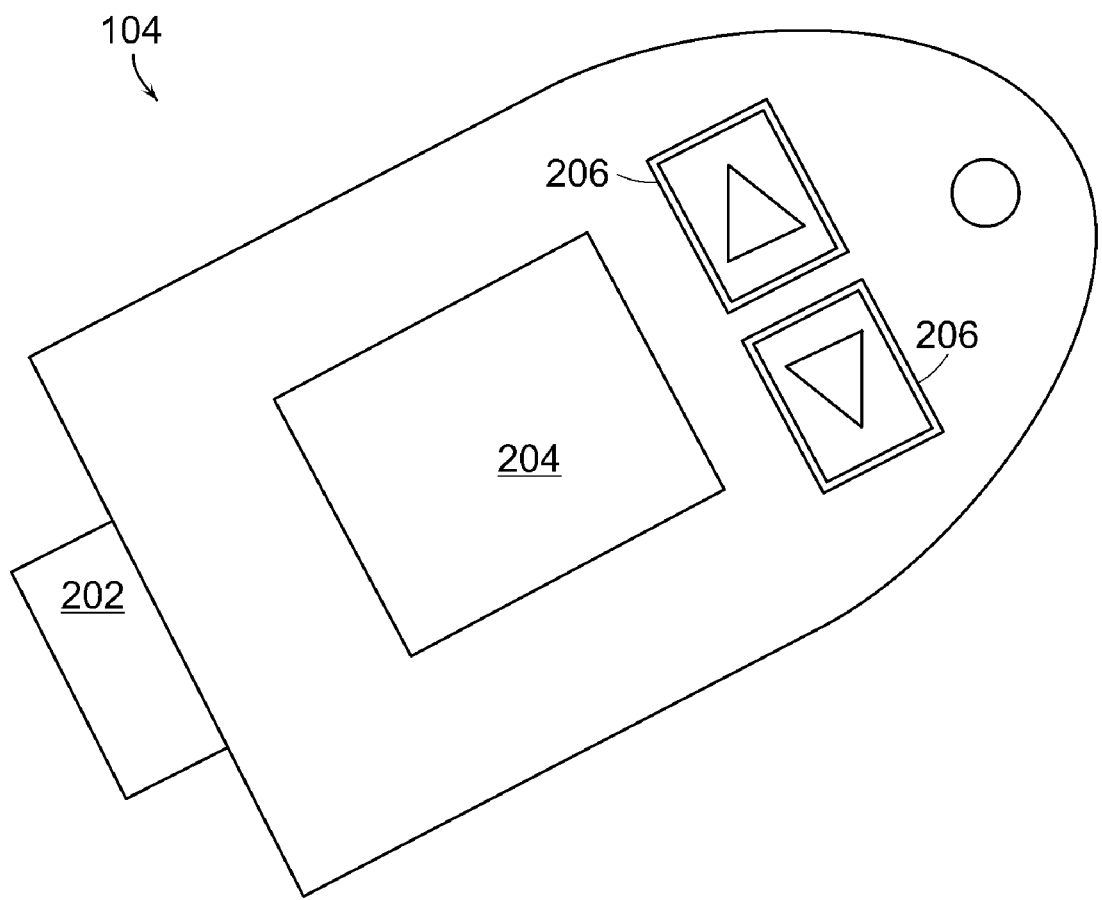
FIG. 2 is an illustration of an exemplary portable memory device for storing personal medical records in accordance with one or more embodiments of the invention.

FIG. 2 illustrates an example of a portable memory device 104. The portable memory device 104 is a small, lightweight, sturdy, preferably water resistant portable device 104 that may look like jewelry and can be carried by a patient, e.g., connected to a key chain or worn. It contains a memory device 104 including, e.g., a nonvolatile flash drive or other form of universal computer memory. The device 104 includes a commonly used or standardized interface 202 that can be operatively coupled to a computer to allow data to be transferred between the memory device 104 and a computer. In this example, the standardized interface 202 is a USB interface. A variety of other standardized interfaces can also be used, including but not limited to, a universal serial port such as Firewire, Serial/RS-232 ports, or wireless interfaces.

The portable memory device 104 is used as a repository for a patient's medical records or, in the case of a family with small children, it can contain the medical records of a parent and one or more children. It contains digital copies of the patient(s)'s medical records accumulated over a lifetime or significant period of time, from multiple care providers. It also preferably stores the patient's contact, employment and insurance information, and family medical history. Additionally, it preferably stores a medical history software application that, when executed by a computer to which the memory device 104 is coupled, enables the patient to update his/her medical history, and enter new problems, complaints and/or information that arise. The memory device 104 also preferably stores a patient record manager software application similar to the care provider's patient record manager that allows the patient, or other party permitted by the patient, to access the portable device 104 to input information and electronically manage, sort and search the patient(s)'s electronic medical records stored on the device 104. The memory device 104 also preferably stores one or more additional software applications that (i) allow data to be uploaded to, and downloaded from, the portable device 104, (ii) automatically link the device 104 to the server to download delayed records and software updates, (iii) encrypt and password control the patient(s)'s medical records, and (iv) facilitate backing up the records to another computer or online backup service.

The portable device 104 also includes a battery-powered display 204, controller mechanism and memory that can be used to access certain critical information about the patient in an emergency without having to connect the portable device 104 to a computer or other power source. This capability may be particularly useful in a power outage or when access to a computer that can be coupled to the device 104 may not be available. A care provider can scroll through the information shown on the display 204 using, e.g., control buttons 206. Access is preferably unrestricted, i.e., anyone in possession of the device 104 can read this limited information, which preferably includes, e.g., the patient's photograph, name, age, language, blood type, medical devices used, past serious illnesses and surgeries, chronic health conditions, allergies, medications, immunizations, emergency contacts, and advance directives.

Access to a patient's medical records stored on the device 104 can be restricted, selectively controlled and protected preferably to more than one level by the use of password(s) or biometric identification. Access to some information preferably is unrestricted, does not require a password and is accessible by anyone in possession of the device 104. As will be described below, such unrestricted information can include critical patient information needed in the event of an emergency and/or if the patient is unable to provide his/her password, such as that which is accessible via the device's display 204 (described above), plus access to the detailed records that underlie the emergency information. Access to most information preferably is restricted and can be retrieved only by entering a secret password provided by the patient (or his/her designated proxy). Such restricted information might include detailed listings of, and access to, notes and records of encounters with care providers and hospitals, diagnostic test reports, images, listings of medications, allergies and immunizations, and extensive personal information. Additionally, if the patient wants to limit access to particularly sensitive medical information such as, e.g., information relating to HIV/AIDS, psychiatric, sexual or other sensitive issues, he or she can protect such records by requiring that the patient (or his/her designated proxy) enter a second different password or reenter the original password to access these records.

The portable memory device 104 preferably prompts persons attempting to access the device 104 to identify themselves and, if required, to enter the patient's password before being given access to the patient's personal health records, and maintains an audit trail identifying all persons accessing the device 104 as well as the records they opened.

The portable memory device 104 is preferably configured to allow storage of data only through the software for managing medical records built into the device 104. Users will preferably not be allowed to install other applications or store other data on the device 104.

The portable device 104 is primarily read-only. Patients and care providers each will be able to selectively enter information and upload records to the device 104, but once information is entered, files stored on the device 104 cannot be altered or deleted. Changes to information stored on the device 104 can preferably be made only by addendum. This read only feature insures the integrity of information stored on the portable memory device 104; it protects both the patient and each care provider from the other changing records after the fact.

Data on the portable memory device 104 and the server 108 are preferably encrypted using an encryption algorithm such as, e.g., MD5, ECC, AES, and SHA-2. Data transferred to and from the portable memory device 104 and server 108 are preferably transferred on an encrypted data channel using an encryption algorithm such as, e.g., SSL and TLS.

Figure 3:
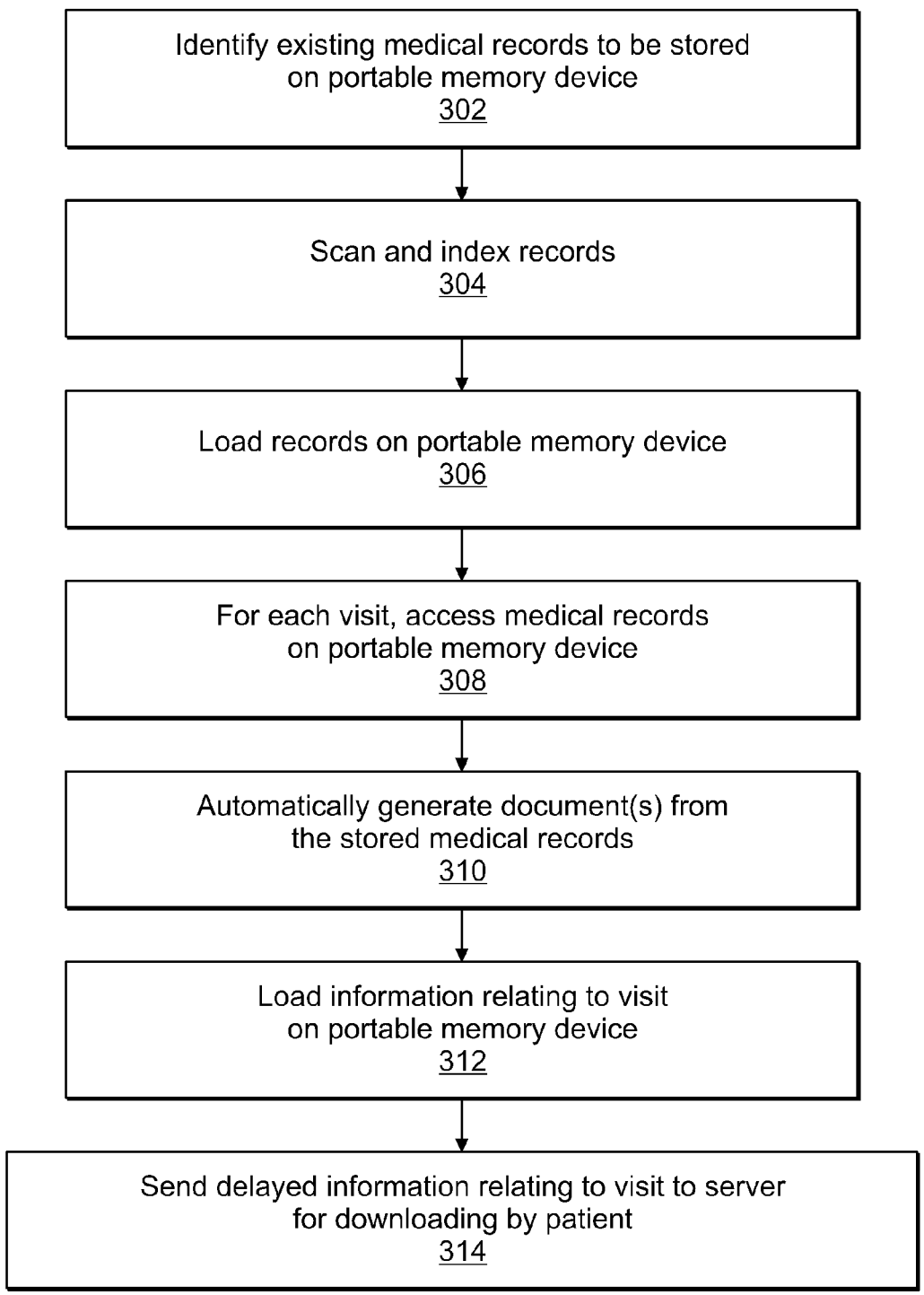
FIG. 3 is a flow chart illustrating a method of managing portable medical records in accordance with one or more embodiments of the invention.

FIG. 3 is a flowchart 300 illustrating usage of the system 100 in accordance with one or more embodiments of the invention. Initially, a portable memory device 104 is dispensed to a patient, e.g., preferably by his or her physician. Each portable memory device 104 includes a unique identifier associated with a particular patient. Personal historical information is entered on the device 104, typically by the patient. Existing medical records of the patient are loaded on the portable memory device 104 by various care providers seen by the patient, by other parties possessing copies of the patient's records, or by the patient himself or herself if the patient has copies of the records. Information and records that have been stored on the portable memory device 104 by a patient are preferably identified as having been entered by the patient. At step 302, care providers determine what past patient records should be stored on the device 104. In some cases, all of the medical records for the patient are selected for storage; in other cases, only a select group of records deemed to be useful in the care of the patient are identified for storage.

Many care providers keep paper patient records. To store these records on the portable memory device 104, the records are converted into digital or electronic form by scanning and indexing. At step 304, the medical records that are in paper form are scanned and indexed for storage. Each record is classified according to one or more index/sorting fields so that the records can be electronically sorted and searched. These index/sorting fields can include but are not limited to: Date of Visit, Care Provider Name, Care Provider Specialty, Reason for Visit/Chief Complaint, CPT (billing code), ICD-9-CM Code (billing code), Anatomical Location and Human Body System of complaint at issue, the type of record (e.g., notes, images, test results, reports, etc.), the type of test or image, and prescription information.

Some care providers keep electronic medical records for their patients. In this case, the patient records to be stored on the portable memory device 104 are in electronic form, and may already be indexed. Additional indexing of these records can be performed if needed.

The scanned, indexed medical records are then loaded on the portable memory device 104 at step 306 by operatively coupling the portable device 104 to the care provider computer system 106 or to a secure device that, in turn, is plugged into the care provider computer system 106, For example, if the portable memory device 104 is a USB flash drive, it can be plugged into the USB port of a care provider computer system 106, allowing files to be easily transferred to the portable memory device 104.

The portable memory device 104 is then given to the patient and preferably is carried or worn by the patient at all times. In this way, the patient retains control over his or her lifetime health care records and has them immediately available when and where a care provider needs them.

At step 308, at each visit to a care provider, the patient presents his or her portable memory device 104 to the care provider (or his or her staff member). The care provider or staff member plugs the device 104 into, or otherwise couples the device 104 to, the care provider's computer system 106 or to a secure device that, in turn, is plugged into the provider computer system 106, and thereby accesses the patient's medical records stored on the device 104.

Care providers can accordingly access the patient's comprehensive lifetime health record to provide proper treatment, avoid medical mistakes, and preclude unnecessary or redundant tests. The care provider can use his/her computer system 106 to sort and search the patient's medical records stored on the portable memory device 104 to identify the patient's known health issues, prior illnesses and treatments, allergies and medications, and to read any relevant underlying clinical notes, charts or images. Because the patient's medical records are stored in electronic form, care providers can perform such sorts and searches virtually instantly and even track a condition's progression over time-tasks that would likely be difficult if the patient's records were not aggregated on a single device in the patient's possession.

Primary care physicians can use a patient's portable memory device 104 to manage the patient's over-all care and prevent conflicting treatments by multiple care providers.

In accordance with one or more embodiments of the invention, a referral document, required by insurers/payers to be issued to a specialist by the referring physician, can be stored on the portable memory device 104 and thereby be available when the patient sees the specialist. This referral document authorizes the specialist to treat the patient; its immediate availability ensures that the specialist is authorized to treat the patient at that initial visit.

Specialists and emergency care providers who have not previously treated the patient, use the patient's portable memory device 104 to understand the patient's condition, determine what tests are needed, and to reduce the possibility that the treatments, prescriptions, and care program they prescribe conflict with those prescribed by others.

At the start of each visit, the care provider or staff member selectively generates one or more documents, at step 310, from the patient's medical records and medical history stored on the portable memory device 104. These documents preferably contain a patient health summary report and a medical encounter report form. The documents can be viewed on a computer screen or personal digital assistant (PDA) or as a copy printed on paper. (As used herein, the term "document" refers both to a digital file that can be viewed on a computer display and to printed material.) The health summary and encounter report forms are created by a report generator built into the software applications, which can reside on the portable memory device 104 or the care provider computer system 106. An example of a patient health summary report is shown in FIGS. 4A and 4B. The health summary report is a form of continuity-of-care document and contains information extracted from the patient's medical records that is expected to be useful by the care providers at the visit. For example, the health summary report can identify the complaint or reason for the current visit, previous medical problems, the patient's current medications, allergies, and recent medical encounter history. Different types of standard or custom summary reports can be generated by the report generator from data stored on the portable medical device 104. For example, summary reports containing appropriate data can be generated for specialists; summary reports containing different data can be generated for hospital admissions. Other summary reports can be generated for special purposes including, e.g., a child's immunization records for school or camp, or information needed by insurance companies. FIG. 4A illustrates an exemplary patient health summary report 402 generated before examination of the patient by the care provider. FIG. 4B illustrates the health summary report 404 after the examination, which reflects information input by a care provider from the examination (in this example, one medication was added and another was discontinued).

An example of a medical encounter report form is shown in FIGS. 5A and 5B. The medical encounter report form can be filled in by the care provider to document the encounter and can constitute the care provider's notes for the encounter if the care provider so chooses, or it can provide the basic information the care provider uses to write or dictate more detailed notes. FIG. 5A illustrates an exemplary encounter report form 502 generated before examination of the patient by the care provider. FIG. 5B illustrates the encounter form 504 containing information input by the care provider from the examination.

The patient health summary and the medical encounter report form are preferably generated on request using software that is stored on the portable memory device 104 or on the care provider's computer system 106. The software extracts pertinent information from the medical records and the patient's medical history stored on the device 104 and automatically populates appropriate fields in the patient health summary and the medical encounter report form. In accordance with one or more embodiments of the invention, the patient health summary and the medical encounter report form are customized for particular care providers. For instance, information pertinent to a specialist care provider may be different from that needed by a primary care provider and, accordingly, different patient health summaries and medical encounter report forms are generated for each. In addition, other medical reports can also be generated for use by patients (such as, e.g., an immunization record, and health information needed to purchase an insurance policy).

At the conclusion of the visit to the care provider, a copy of the care provider's record of the visit is uploaded and stored by the care provider or his or her staff member on the patient's portable memory device 104, at step 312. The care provider or staff member then returns the portable memory device 104 to the patient.

Any delayed information relating to the visit (i.e., information not available at the time the patient leaves the premises such as, e.g., transcribed notes or lab test results) is uploaded by the performing-care provider to the server computer system 108, at step 314. These delayed records are stored on the server 108 until the patient downloads them, whereupon they are preferably deleted from the server. The performing-care provider can upload the delayed information through the website hosted by the server computer system 108. Alternatively, the performing-care provider can send the delayed information by facsimile or mail to the server computer system.

Pharmacies, upon filling a prescription, can upload information about the prescription, such as name of patient, medication, dosage, frequency, prescribing care provider, number of renewals, etc., to the server computer system 108 for the patient's account. These data can be transmitted directly over the Internet or wirelessly from the pharmacy's computer system or other input/output device. Such data also can be obtained indirectly from a communication service transmitting prescription information between a pharmacy and the prescribing care provider. These delayed records are stored on the server 108 until the patient downloads them, whereupon they are preferably deleted from the server.

The server computer system 108 preferably sends notification (e.g., by e-mail) to the patient and the ordering-care provider whenever any delayed patient records are available to be downloaded on the patient's portable memory device 104. The patient and ordering-care provider can access the records through the website maintained by the server computer system. In a preferred embodiment, the portable memory device 104 includes synchronization software that automatically establishes a connection between the patient's computer system 102 and the server computer system 108 whenever the portable memory device 104 is coupled to an Internet-connected computer, and automatically downloads any available patient records and system updates onto the portable memory device 104.

Patients preferably periodically back up data stored on their portable memory devices 104 to avoid the risk of losing their data if the portable memory device 104 fails, or is lost or damaged. Patients may back up their data to their personal computers 102 whereby an encrypted file containing the medical record information will be placed on the patient's computer 102. That information is preferably both password protected and encrypted, e.g., at a minimum of 128 bit encryption. The data stored on the patient's computer 102 can be resynchronized to any new patient memory device 104 through a restore interface. After the encrypted data are exported to the patient's computer 102 from the patient's memory device 104, it can be uploaded to a remote backup facility on the Internet such as, e.g., carbonite or .mac. Alternatively, the patient's memory device 104 can be connected to the Internet through any Internet enabled computer to back up the data directly. Once plugged into the computer the patient can backup the memory device 104 via a backup interface. The backed up patient record is an encrypted and password protected file and is automatically stored in the patient's backup repository.

Alternatively, the patient's care provider or staff member can back up the patient's records, if desired, to their care provider's computer system 106. The care provider computer system 106 preferably includes a dedicated backup computer residing in the care provider office used exclusively for backing up records from patients' portable memory devices 104. The backup computer preferably has no function other than to back up and restore data on patients' portable memory devices 104. To back up data from a portable memory device 104, the portable memory device 104 is operatively coupled to a port on the backup computer. Data stored on the portable memory device 104 can then be automatically uploaded to the backup computer for storage. Additionally, data on the backup computer can be used to restore data to a patient's portable memory device 104. Backed up data preferably are encrypted so no one, including the care provider providing this backup service, can access or read patient records.

In addition, the server computer system 108 can be configured to provide long term backup storage of patient records. Patients can accordingly back up their records, if desired, to the server computer system 108 by accessing the server computer system 108 through a web portal. This backup operation can be performed whenever the patient elects to do so or, alternatively, whenever the patient connects to the server 108.

Figure 6:
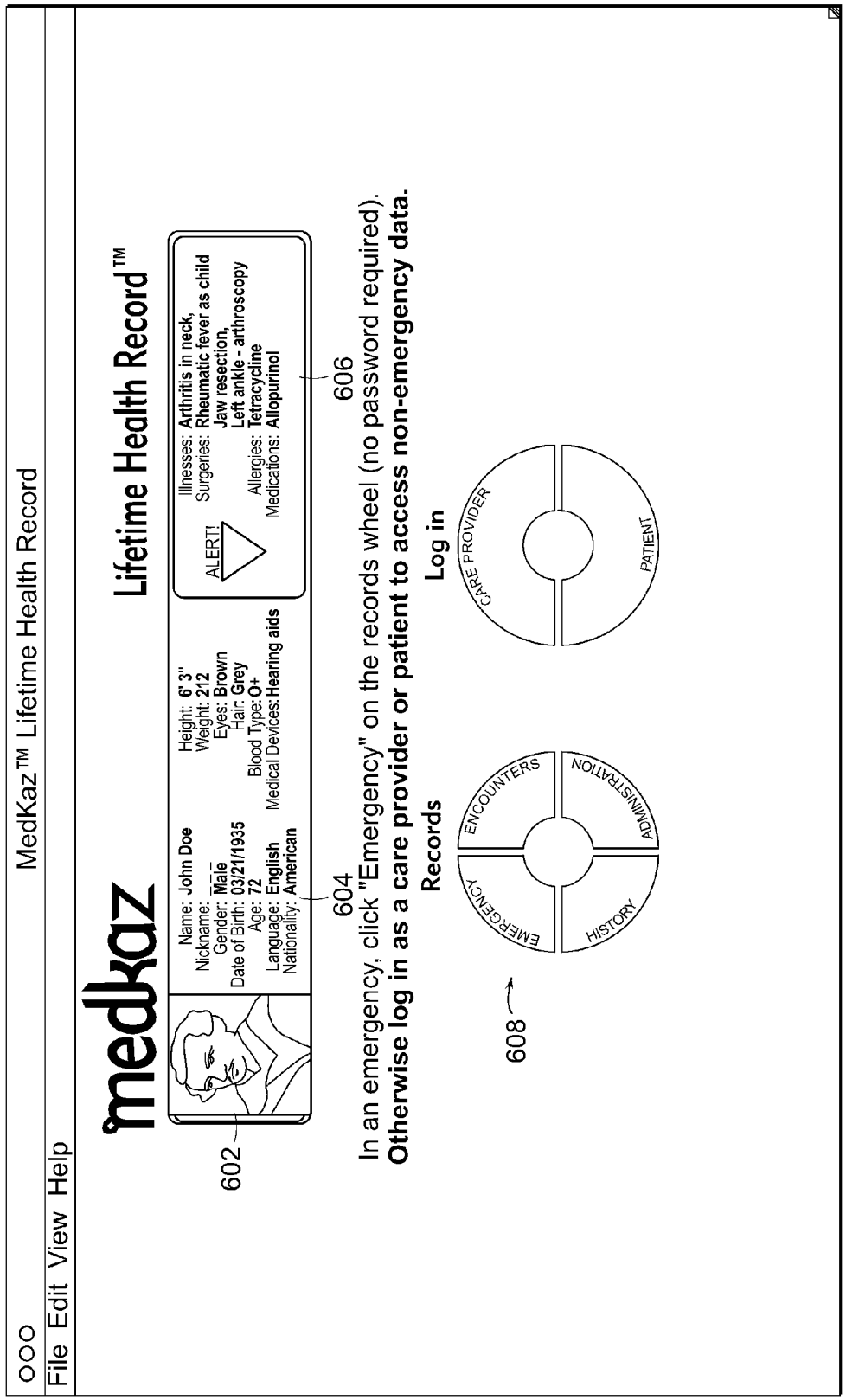
FIG. 6 is an exemplary screenshot illustrating information displayed to a user initially accessing a portable memory device in accordance with one or more embodiments of the invention.

FIG. 6 is an exemplary screenshot 600 illustrating information displayed on the care provider computer system 106 when a care provider initially accesses the portable memory device 104. The screenshot includes a photograph 602 of the patient and personal information 604 about the patient. Also displayed is critical information 606 about the patient including past serious illnesses, surgeries, allergies, and medications. The data stored on the portable memory device 104 can be organized for ease of use into several categories, e.g., emergency information, encounter information, patient history information, and administration information. Each of these categories can be accessed by selecting corresponding virtual buttons 608. Unrestricted access is provided to the emergency information. However, access to other information can only be obtained by entering a designated password after logging in using buttons by the care provider or the patient.

Once a care provider has logged in, he or she can be provided a menu (not shown) allowing the care provider to (1) create reports (including health summary reports (as shown, e.g., in FIG. 4A), encounter forms (as shown, e.g., in FIG. 5A), and other special reports), (2) view an anatomical screen interface (as shown, e.g., in FIG. 8), or (3) perform patient memory device backup or restoration.

Once a patient has logged on, he or she can be provided a menu (not shown) allowing the patient to (1) enter data on his or her portable memory device (including data on Current Condition, Historical/Administrative Information Addendum, and Personal Home Health Data), and (2) perform memory device backup/restoration to/from the patient's own computer, an online computer backup service, or the server 108.

In accordance with one or more embodiments of the invention, a care provider seeking to access information on the memory device 104 is required to log in and enter a care provider identifier (such as a unique identifier associated with the care provider in a national care provider directory). This information is used to verify that the physician is properly licensed, and is entered in a log constituting an audit trail indicating who has accessed the device 104 and the documents they accessed.

FIG. 7 illustrates exemplary encounter information 700 displayed upon selection of the "Encounters" button 608. As shown in this figure, the encounter information is organized into three subcategories: Doctors-Dentists-Hospitals, Tests-Labs & Images, and Pharmacies & Physical Therapy. Each subcategory, in turn, is organized according to various categories. The Doctors-Dentists-Hospitals subcategory in this figure includes categories headed: Date, Practitioner, Specialty, Reason/Chief Complaint, CPT, Assessment/Procedure, ICD-9-CM Code, Document Type, Anatomical Location, and Body System. The user can sort the encounter information according to any of the categories by selecting the category heading. Each of the encounter entries also indicates whether there is available linked documentation related to that encounter. In this example, a paper clip symbol or other type of symbol 702 indicates the availability of this documentation. Selecting an entry with a paper clip causes the available underlying document (such as, e.g., a medical examination report or lab test report) to be displayed to the user. Access to some documentation can be restricted. In this case another symbol such as, e.g., a padlock 704 can be used to indicate that a second password entry is needed to access the underlying document(s).

In the exemplary screenshots, a colored paperclip indicates that the document is text searchable. Accordingly, the physician can search for keywords within a document. In addition, the physician can search for keywords through all documents stored on the portable memory device 104 that are text searchable. Typed and/or electronic documents that are not text searchable can be made into a searchable document using, e.g., optical character recognition. All documents including handwritten documents can be sorted by selecting the various indexing/sorting field headings, e.g., anatomical location.

Another screen that can be accessed (not shown) provides a listing of images and test/lab result information relating to encounters. The user can select and view an image or test/lab results stored on the memory device 104 as desired.

Another screen that can be accessed (not shown) can illustrate pharmacy and physical therapy information stored on the memory device 104.

Figure 8:
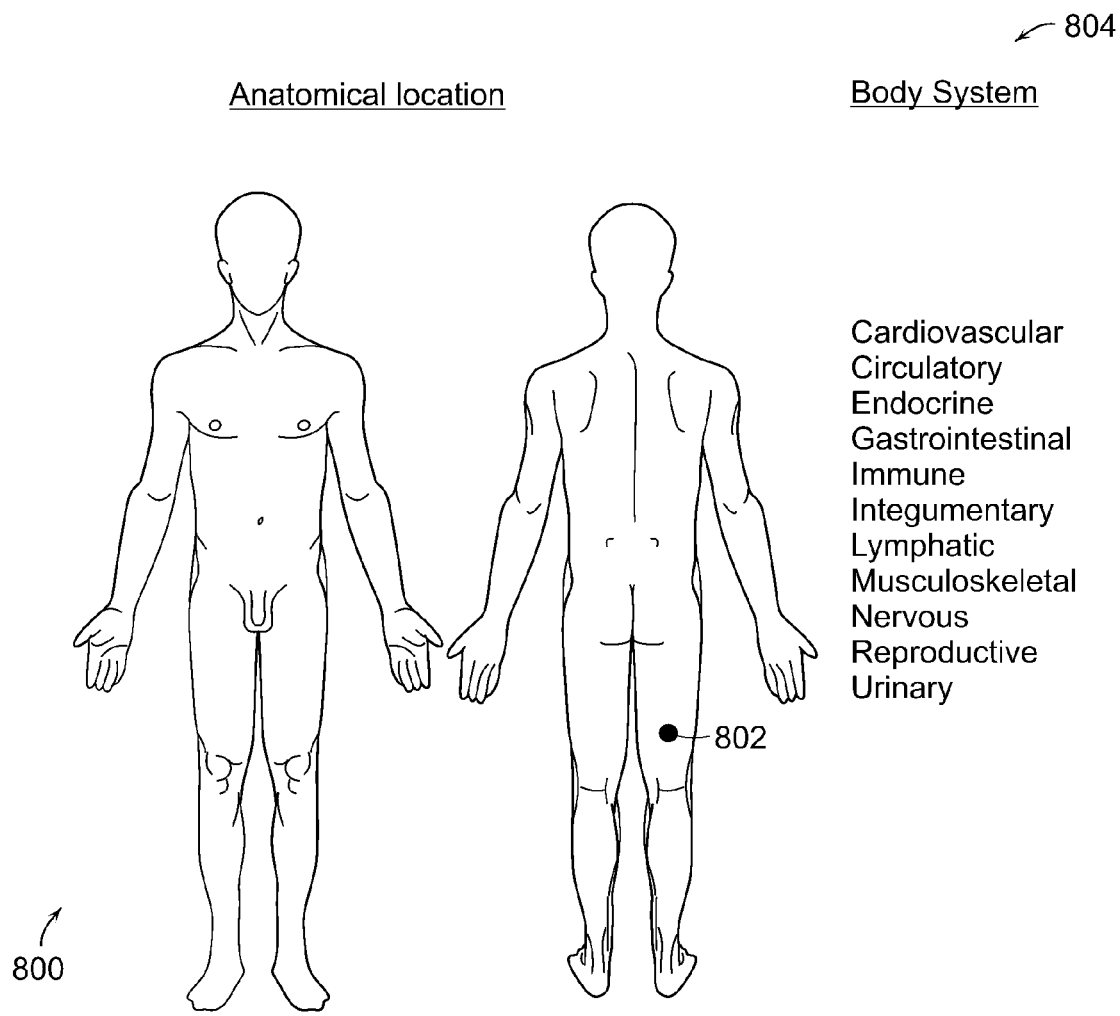
FIG. 8 is an exemplary screenshot illustrating an anatomical location and listing of human body systems interface for accessing records stored on the portable memory device in accordance with one or more embodiments of the invention.

FIG. 8 is a screenshot illustrating an exemplary anatomical diagram interface 800, which allows the user to quickly and easily identify all medical records for a patient relating to a particular anatomical location and/or body system. Different anatomical diagrams can be used to portray men, women, boys, girls, and small children. Anatomical locations on the diagram are highlighted by a marking (in this example a dot 802) to indicate that there are indexed medical records for the patient relating to that anatomical location. The user can point to and select a highlighted anatomical location in the drawing using a mouse or other pointer device, which will cause a listing to be displayed with all records categorized by that anatomical location. Similarly, the interface 800 includes a list 804 of body systems that can be selected by the user to identify all patient records applicable to that body system.

Additional screens (not shown) can show emergency information stored on the memory device 104 and displayed upon selection of emergency button 608. Information provided can include an identification of past serious illnesses, surgeries, chronic conditions and medical devices used by the patient. Emergency information can also include current medications, allergies, and immunizations. In addition, emergency information subcategories can also identify family contact information and advance directives.

Additional screens (not shown) can show administration information stored on the memory device 104 and displayed upon selection of administration button 608. Information displayed can include patient contact information, insurance information, and responsible party information. Other administrative information subcategories can include information about the patient's care providers and employers.

Additional screens (not shown) can show patient and family history information stored on the memory device 104 and displayed upon selection of a family history button. Information displayed can include subcategories such as social history, early history, and family history information.

In accordance with one or more further embodiments of the invention, the software on the portable memory device 104 can access external databases to learn about prescribed medications and to determine if medications prescribed by the physician conflict with other medications taken by the patient. For example, a drug prescribed by the physician may have an adverse reaction with another drug currently taken by the patient. The software on the portable memory device 104 can identify any medication conflicts and alerts the patient or the physician.

In accordance with one or more further embodiments of the invention, the software on the portable memory device 104 can assemble data from reports containing similar data and/or test results and generate a chart or table plotting the progression of certain measurements over time. For example, the software can collect a patient's cholesterol readings from annual test reports and create a consolidating report showing how cholesterol readings have changed over time.

In accordance with one or more further embodiments of the invention, the column headings included as indexing or sorting fields may include a column for data provided by other parties or other care provider records, such as the cost of each encounter, thereby permitting the patient to determine the total cost of care relating to a particular illness or condition. Such cost data can be obtained from the claims filed by care providers with the patient's health plan or payer.

In accordance with one or more further embodiments of the invention, the portable memory device 104 can be used as a portal to collect and transmit to the server data from devices used by patients at home or elsewhere that measure/monitor and report body functions and/or systems, e.g., blood sugars, weight, blood pressure, temperature, diet intake, pacemakers/defibrillators, peak flows, INR-PT, etc. Software on the portable memory device 104 can contain tooling to record patient entered data, e.g., from an at-home device that measures the blood sugar count. The patient can enter these test data into the tooling over time. The software can generate a report (including, e.g., a chart or table plotting the progression of certain measurements over time), which can be made available to care providers.

The portable memory devices 104 preferably contain a log that details every transaction (e.g., the loading of data and data access) made, by whom, and the documents accessed. The information contained in the log is preferably synchronized with the computer server 108. Once the data are in the server 108, it can be used for technical, business, and marketing purposes. For example, the log information can be used to compile statistical and analytical reports on transaction volume, who is uploading and downloading information from the portable memory device 104 and the server 108, problems care providers are having using the portable memory device 104 and/or server 108, the number and types of transactions being reported, and for accounting purposes including tracking payments owed to or from care providers, The log information also can be analyzed to determine which modules or features of the system are being used or not used, user patterns, and which markets are strong or weak.

The log information can be analyzed to determine if the portable memory device is being used correctly per instructions, and to identify applications on the portable memory device 104, the server 108 or the system in general which should be improved, revised, discontinued, upgraded and/or expanded.

In accordance with one or more embodiments of the invention, the portable memory device preferably contains one or more training videos or demos showing care providers and/or staff members how to use the portable memory device, e.g., how to create report documents such as the health summary, encounter report form and referral documents; how to scan a document, add the requisite index/sorting field data, and upload it to the portable memory device 104 or server 108; and how to back up a patient's portable memory device to the care provider's computer system 106.

It is to be understood that although the invention has been described above in terms of particular embodiments, the foregoing embodiments are provided as illustrative only, and do not limit or define the scope of the invention. Various other embodiments also fall within the scope of the claims. For example, elements, components, and functionality of the computer systems described herein may be further divided into additional components or joined together to form fewer components for performing the same functions.

The methods described above are preferably implemented in software, and accordingly one of the preferred implementations of the invention is as a set of instructions (program code) in a code module resident in the random access memory of the computer. Until required by the computer, the set of instructions may be stored in another computer memory, e.g., in a hard disk drive, or in a removable memory such as an optical disk (for eventual use in a CD ROM) or floppy disk (for eventual use in a floppy disk drive), or downloaded via the Internet or some other computer network. In addition, although the various methods described are conveniently implemented in a general purpose computer selectively activated or reconfigured by software, one of ordinary skill in the art would also recognize that such methods may be carried out in hardware, in firmware, or in more specialized apparatus constructed to perform the specified method steps.

Having described preferred embodiments of the present invention, it should be apparent that modifications can be made without departing from the spirit and scope of the invention.

Method claims set forth below having steps that are numbered or designated by letters should not be considered to be necessarily limited to the particular order in which the steps are recited.

What is claimed is:

1. A method, for care providers in the course of treating patients, of utilizing indexed copies of medical records from multiple care providers stored on portable memory devices owned and controlled by the patients, and for indexing, assembling, and updating the patients' medical records and patient information on their portable memory devices, each portable memory device aggregating and storing actual copies of a patient's medical records irrespective of how they are formatted or stored on care providers' paper or disparate electronic systems, said medical records on the portable memory devices being sortable, searchable, readable, and cross-platform compatible, for each encounter with a patient, the method comprises the steps of:

(a) accessing the medical records on the patient's portable memory device, wherein access to the medical records stored on the portable memory device is controlled to at least three levels, including a first level of unrestricted access to limited information for emergency providers, a second level of password-protected access to a given set of medical records, said given set of medical records including medical information on said patient that is different from said limited information, and a further third level of password-protected access to a set of patient-designated sensitive medical records, said set of patient-designated sensitive medical records including medical information on said patient that is different from said limited information and from said given set of medical records;

(b) generating a pre-populated health summary report derived from the medical records of multiple encounters or patient history stored on the patient's portable memory device;

(c) generating a pre-populated referral document derived from the medical records stored on the patient's portable memory device and storing the referral document on the portable memory device to be provided to a specialist care provider along with medical records of the patient stored on the portable memory device, wherein said referral document authorizes the specialist care provider to treat the patient;

(d) generating an encounter summary report form partially pre-populated with data derived from the medical records stored on the patient's portable memory device, and recording data on the encounter summary report form relating to the patient's health developed during the encounter, wherein the pre-populated data includes the date, patient's name, and complaints or reasons for the visit, and wherein the data recorded on the encounter summary report form includes the care provider's assessment of the patient's condition, the billing codes applicable to the visit, and the anatomical locations and body systems that were the subject of the visit;

(e) sorting or searching through copies of the medical records stored on the portable memory device using indexing fields to find and retrieve specific scanned images of underlying medical documents stored on the portable memory device, said medical records being sortable based on a plurality of criteria; and (f) updating the patient's medical records on the portable memory device during or following the encounter by scanning and indexing paper records and indexing electronic records, and uploading the indexed records irrespective of their original formats to the patient's portable memory device and the care provider's patient record manager as electronically-manageable records.

2. The method of claim 1 further comprising automatically generating a report on allergies, a report on current medications taken by the patient, an immunization report, an insurance application report, a referral authorization document, or a hospital admission report from the indexed medical records stored on the portable memory device.

3. The method of claim 1 wherein searching through the medical records comprises using an anatomical location interface and an interface listing human body systems that are the subject of each encounter with a care provider linked to associated indexed medical records stored on each of said portable memory devices to electronically identify a record of interest from a plurality of medical records stored on the portable memory device.

4. The method of claim 1 further comprising periodically backing up medical records that are stored on a portable memory device.

5. The method of claim 1 further comprising generating a report from data stored on said portable memory device illustrating progression of one or more health related measurements over a given period of time.

6. The method of claim 1 further comprising using a patient record manager for a care providers to use to electronically store, manage, access, sort, and search encounter records for a plurality of patients treated by the care provider.

7. The method of claim 1 wherein said patient information includes the patient's personal, demographic, contact, and insurance information.

8. The method of claim 1 wherein said health summary draws data from medical records from more than one encounter contained on the patient's device and is used by the care provider to record serious health problems and medications the care provider has instructed the patient to stop taking and new medications to start taking 9. The method of claim 1 wherein the plurality of criteria on which said medical records are sortable include date, practitioner name, specialty, reason/complaint, assessment/procedure, billing codes, document type, or anatomical locations or body systems that are the subject of the visit.

10. The method of claim 1 further comprising the step of storing on the portable memory device cost of care data relating to each encounter to permit the total cost of care related to a particular illness or condition to be determined.

11. The method of claim 1, wherein the patient's portable memory device stores an audit trail identifying persons who have accessed the portable memory device and the records they opened.

12. A method for managing portable patient medical records, comprising:

(a) providing a portable memory device to each of a plurality of patients for electronically storing indexed medical records for said patient from a plurality of care providers, wherein care providers utilize the indexed copies of medical records in the course of treating patients, and index, assemble, and update the patients' medical records and patient information on their portable memory devices, each portable memory device aggregating and storing actual copies of a patient's medical records irrespective of how they are formatted or stored on care providers' paper or disparate electronic systems, said medical records on the portable memory devices being sortable, searchable, readable, and cross-platform compatible, wherein for each encounter with a patient, a care provider can utilize the patient's portable memory device to: (i) access the medical records on the patient's portable memory device, wherein access to the medical records stored on the portable memory device is controlled to at least three levels, including a first level of unrestricted access to limited information for emergency providers, a second level of password-protected access to a given set of medical records, said given set of medical records including medical information on said patient that is different from said limited information, and a further third level of password-protected access to a given set of patient-designated sensitive medical records, said set of patient-designated sensitive medical records including medical information on said patient that is different from said limited information and from said given set of medical records; (ii) generate a pre-populated referral document created by a referring physician and a health summary report derived from the medical records of multiple encounters or patient history stored on the patient's portable memory device wherein said referral document authorizes a specialist care provider to treat the patient; (iii) generate an encounter summary report form partially pre-populated with data derived from the medical records stored on the patient's portable memory device, and record data on the encounter summary report form relating to the patient's health developed during the encounter, wherein the pre-populated data includes the date, patient's name, and complaints or reasons for the visit, and wherein the data recorded on the encounter summary report form includes the care provider's assessment of the patient's condition, the billing codes applicable to the visit, and the anatomical locations and body systems that were the subject of the visit; (iv) sort or search through copies of the medical records stored on the portable memory device using indexing fields to find and retrieve specific scanned images of underlying medical documents stored on the portable memory device, said medical documents being sortable based on a plurality of criteria; and (v) update the patient's medical records on the portable memory device during or following the encounter by scanning and indexing paper records and indexing electronic records, and upload the indexed records irrespective of their original formats to the patient's portable device and the care provider's patient record manager as electronically-manageable records; and (b) for each visit to a care provider by a patient:
(i) receiving from the care provider delayed information relating to medical services previously provided by the care provider to the patient or relating to laboratory, radiology, or pharmacy services; and
(ii) transmitting said delayed information to a computer operated by the patient or another authorized person for subsequent downloading of said delayed information by said patient or another authorized person from said computer to the portable memory device of the patient.

13. The method of claim 12 further comprising sending notification to said patient or another authorized person or an ordering-care provider of receipt of delayed information relating to medical services previously provided to the patient by a care provider or relating to laboratory, radiology, or pharmacy services, and subsequently enabling retrieval of the delayed information by said patient or another authorized person or said ordering-care provider from a website operated by a server computer system.

14. The method of claim 12 wherein each portable memory device stores a log of transactions for said portable memory device, and wherein the method further comprises receiving said log and performing a business, marketing, or technical analysis of said log, and determining if the applications on the device should be improved, revised, discontinued, upgraded, or expanded.

15. The method of claim 12 further comprising receiving data from a medications database or network, and said data is used to determine if medications prescribed by a care provider would cause an adverse reaction with other medications taken by the patient stored on the portable memory device.

16. The method of claim 12 further comprising automatically delivering software updates to said portable memory devices.

17. The method of claim 12 further comprising backing up data from said portable memory devices.

18. A system for managing portable patient medical records, comprising:
a plurality of portable memory devices, each to be provided to one of a plurality of patients for electronically storing indexed copies of medical records for said patient from a plurality of care providers, wherein care providers utilize the indexed copies of medical records in the course of treating patients, and index, assemble, and update the patients' medical records and patient information on their portable memory devices, each portable memory device aggregating and storing actual copies of a patient's medical records irrespective of how they are formatted or stored on care providers' paper or disparate electronic systems, said medical records on the portable memory devices being sortable, searchable, readable, and cross-platform compatible, wherein for each encounter with a patient, a care provider can: (a) access the medical records on the patient's portable memory device, wherein access to the medical records stored on the portable memory device is controlled to at least three levels, including a first level of unrestricted access to limited information for emergency providers, a second level of password-protected access to a given set of medical records, said given set of medical records including medical information on said patient that is different from said limited information, and a further third level of password-protected access to a given set of patient-designated sensitive medical records, said set of patient-designated sensitive medical records including medical information on said patient that is different from said limited information and from said given set of medical records; (b) generate a pre-populated referral document created by a referring physician and a health summary report derived from the medical records of multiple encounters or patient history stored on the patient's portable memory device, wherein said referral document authorizes a specialist care provider to treat the patient; (c) generate an encounter summary report form partially pre-populated with data derived from the medical records stored on the patient's portable memory device, and record data on the encounter summary report form relating to the patient's health developed during the encounter, wherein the pre-populated data includes the date, patient's name, and complaints or reasons for the visit, and wherein the data recorded on the encounter summary report form includes the care provider's assessment of the patient's condition, the billing codes applicable to the visit, and the anatomical locations and body systems that were the subject of the visit; (d) sort or search through copies of the medical records stored on the portable memory device using indexing fields to find and retrieve specific scanned images of underlying medical documents stored on the portable memory device, said medical records being sortable based on a plurality of criteria; and (e) update the patient's medical records on the portable memory device during or following the encounter by scanning and indexing paper records and indexing electronic records, and upload the indexed records irrespective of their original formats to the patient's portable device and the care provider's patient record manager as electronically-manageable records; and a computer server for (i) receiving delayed information from the plurality of care providers for each visit by a patient to a care provider, said delayed information relating to medical services previously provided to the patient by the care provider or relating to laboratory, radiology, or pharmacy services; and (ii) transmitting said delayed information to a computer operated by the ordering-care provider or to a computer operated by the patient or another authorized person for subsequent downloading of said delayed information by said patient or another authorized person from said computer to said portable memory device.

19. The system of claim 18 wherein said computer server further receives from each portable memory device a log of transactions for said portable memory device, and performs a business, marketing, or technical analysis of said log.

20. The system of claim 18 wherein said computer server further receives data from a medications database, said data used to determine potential adverse reactions between medications prescribed by a care provider and medications taken by the patient stored on the portable memory device.

21. The system of claim 18 wherein said computer server further automatically delivers software updates to said portable memory devices.

22. The system of claim 18 wherein each of said portable memory devices includes a standardized interface selected from the group consisting of a USB port, a Firewire port, a Serial/RS-232 port, and a wireless interface, and wherein each portable memory device includes a flash drive or other standardized storage device.

23. The system of claim 18 wherein each of the portable memory devices includes a display for showing selected information relating to the patient associated with said portable memory device, and a control mechanism for operating said display.

24. The system of claim 18 wherein anatomical location and human body system interfaces linked to said indexed medical records are stored on each of said portable memory devices for enabling care providers to electronically identify a record of interest from a plurality of medical records stored on the portable memory devices.

25. The system of claim 18 wherein said computer server periodically backs up medical records from all the patient's care providers stored on a portable memory device to facilitate recovery in the event of loss or failure of the portable memory device.

26. The system of claim 18 wherein medical records stored by each portable memory device are read-only and undeletable, and wherein additional information or corrections to a medical record can be added by addendum.

27. The system of claim 18 wherein said portable memory devices store a training video or demo on use of the device.

28. The system of claim 18 further comprising a patient record manager for each of a plurality of care providers to use to electronically store, manage, access, sort, and search medical records for a plurality of patients treated by the care provider.

29. The system of claim 18 wherein said computer server further notifies said patient or another authorized person or an ordering-care provider of receipt of delayed information and provides access to the delayed information from a website operated by the computer server.

* * * * *